United States Patent [19]
Attfield

[11] Patent Number: 5,891,653
[45] Date of Patent: *Apr. 6, 1999

[54] METHOD OF SUPPRESSING GRAFT REJECTION BY MEANS OF STRESS PROTEINS

[76] Inventor: Derrick Cecil Attfield, 1568 Bellaire Pl., Pittsburgh, Pa. 15226-1910

[*] Notice: This patent issued on a continued prosecution application filed under 37 CFR 1.53(d), and is subject to the twenty year patent term provisions of 35 U.S.C. 154(a)(2).

[21] Appl. No.: 774,038

[22] Filed: Dec. 27, 1996

Related U.S. Application Data

[60] Provisional application No. 60/012,959 Dec. 29, 1995.
[51] Int. Cl.$^6$ .......................... G01N 33/567; A61K 38/00
[52] U.S. Cl. ............................ 435/7.21; 530/868; 514/21
[58] Field of Search ............................... 514/21; 530/868; 435/7.21

[56] References Cited

U.S. PATENT DOCUMENTS 5,348,945  9/1994  Berberian et al. .......................... 514/21

*Primary Examiner*—Jeffrey Stucker
*Assistant Examiner*—Hankyel T. Park
*Attorney, Agent, or Firm*—Webb Ziesenheim Bruening Logsdon Orkin & Hanson, P.C.

[57] ABSTRACT

The present invention describes the application of specifically derived stress proteins in the modulation of certain specific immune responses in the human and animal body. This application under certain conditions may require the in vitro (out of body) treatment of certain tissues (including cells of all lineages) derived from the intended recipient body or specific donor body, in the case of organ or cell transplantation. The intracellular activity and the subsequent protection against mortality in a cell or tissue has been described in another U.S. patent, U.S. Pat. No. 5,348,945 entitled "Method of treatment with HSP70". The present invention differs from the aforementioned patent in that it does not describe a method for non-specific or specific protection against mortality. The invention may be employed to suppress allograft rejection and the rejection of xenografts, transplanted into human and/or animals.

16 Claims, No Drawings

METHOD OF SUPPRESSING GRAFT REJECTION BY MEANS OF STRESS PROTEINS

This application is a Continuation-In-Part of Provisional patent application Ser. No. 60/012,959.

FIELD OF THE INVENTION

The present invention relates to the use of stress proteins derived from specific human or animal cells or tissues or cells of any other origin (Prokaryotic, Eukaryotic or Plant) genetically engineered to express human or animal proteins or characteristics, to modulate the immune response of humans or animals. The immune response is to mean any condition inside or outside the body where an invading organism whether bacterial, viral or parasitic is combatted by the host (human or animal) tissues or specialized cells. It also includes any response by the host (human or animal) tissues or specialized cells mounted against or in favor of any allo-, auto- or xeno-transplanted tissues or cells. This modulation is understood to be the result of in vivo or in vitro (in body or out of body) treatment of host tissues or specialized cells with these specifically derived stress proteins.

BACKGROUND OF THE INVENTION

Stress proteins are a very highly conserved group of proteins (Schlesinger, M. J. (1994) "How the Cell Copes with Stress and the Function of Heat Shock Proteins," *Pediatric Research*, 36(1 Pt 1): 1–6). This term, stress protein, includes both heat shock proteins and glucose regulated proteins and other candidate proteins, such as Erp72. Certain members of the stress proteins are constitutively expressed and are essential components of the cellular machinery. Other members of the group are not readily detectable under normal circumstances but in situations of stress and injury, such as ischemia, (Perdrizet, G. A., Kaneko, H., et al. (1993) "Heat shock and recovery protects renal allografts from warm ischemic injury and enhances hsp72 production," *Transplantation proceedings* 25(1 Pt 2): 1670–3), hyperthermia. (Chatson, G., Perdrizet, G., et al. (1990) "Heat shock protects kidneys against warm ischemic injury," *Current Surgery* 47(6): 420–3), physical trauma, reperfusion injury, the expression of these proteins are greatly upregulated (Currie, R. W., White, F. P. (1981) "Trauma-induced protein in rat tissues: a physiological role for a 'heat shock' protein?" *Science* 214(4516): 72–3). Some of these proteins are also specifically upregulated by treatment of cells of almost any origin, with various chemical and physical agents, such as arsenite, radiation, UV light exposure, chemical compounds including Calcium Ionophore A23187 (Resendez, Jr., E., Attenello, J. W., et al. (1985) "Calcium ionophore A23187 induces expression of glucose-regulated genes and their heterologous fusion genes" *Molecular & Cellular Biology* 5(6): 1212–9). The existence of the heat shock response which causes the expression of these stress proteins was initially described in 1962 with the observation that Drosophila salivary gland chromosomes puffed when exposed to supraphysiological temperatures (Ritossa, F. M. (1962) "A new puffing pattern induced by a temperature shock and DNP in Drosophilal" *Experientia* 18: 571–573). When the existence of the stress proteins were discovered it became apparent that by inducing the expression of these proteins in a cell it may lead to increased resistance of the cell to similar stresses (Tissieres, A., Mitchell, H. K., et al. (1974) "Protein synthesis in salivary glands of Drosophila melanogaster: relation to chromosome puffs" *Journal of Molecular Biology* 84(3): 389–98). The stress proteins as a group are however also intricately involved in the process of antigen presentation by cells of all types in the human and animal organism or body (Williams, DB, W. T. (1995) "Molecular chaperones in antigen presentation" *Current Opinion in Immunology* 1(7): 77–84; Li, Z. and Srivastava, P. K. (1994) "A critical contemplation on the role of heat shock proteins in transfer of antigenic peptides during antigen presentation" *Behring Institute Mitteilungen* (94): 37–47; Udono, H. and Srivastava, P. K. (1993) "Heat shock protein 70-associated peptides elicit specific cancer immunity" *Journal of Experimental Medicine* 178(4): 1391–6; Mariethos, E., Tacchini-Cottier, F., et al. (1994) "Exposure of monocytes to heat shock does not increase class II expression but modulates antigen-dependent T cell responses" *International Immunology* 6(6): 925–930; Hightower, L. E., Sadis, S. E., et al. (1994) "Interactions of vertebrate hsc70 and hsp70 with unfolded proteins and peptides" *The Biology of Heat Shock Proteins and Molecular Chaperones*. R. L. Morimoto, A. Tissieres and C. Georgopoulos. Plainview, N.Y., Cold Spring Harbor Laboratory Press: 179–208; Buskirk, A. V., Crump, B. L., et al. (1989) "A peptide-binding protein having a role in antigen presentation is a member of the HSP70 heat shock protein family" *J. Exp. Med.* 179: 1799; and Ryan, C., Stevens, T. H., et al. (1992) "Inhibitory effects of hsp70 chaperones on nascent polypeptides" *Protein Science* 1(8): 980–5). Evidence has been presented to support the possibility that these proteins may also be secreted or released in the immediate environment of the stressed cell or tissue (Hightower, L. E., Guidon, Jr., P. T., (1989) "Selective release from cultured mammalian cells of heat-shock (stress) proteins that resemble glia-axon transfer proteins" *Journal of Cellular Physiology* 138(2): 257–66). Experimental data has also shown that there is reason to believe that secreted or released stress proteins can once again be ingested by a number of other specialized cells including macrophages (Suto, R. and Srivastava, P. K. (1995) "A Mechanism for the Specific Immunogenicity of Heat Shock Protein-Chaperoned Peptides" *Science* 269 (Sep. 15, 1995): 1585–1588) and dendritic cells (own data).

The allo-immune response is dependent on the recognition by host cytotoxic lymphocytes of allo-MHC (Major Histo Compatibility) molecule and donor peptide complexes. This recognition has to lead to an effector response to cause rejection of an allograft or xenograft, although other mechanisms may also be important in xenotransplant rejection. This recognition and response is dependent on activation of donor MHC complex specific host T-lymphocytes by donor derived antigen presentation cells (including macrophages and dentritic cells and possibly other cell types) or specific subsets of donor antigen presenting cells (Thomas, R., Davis, L. S., et al. (1993) "Comparative accessory cell function of human peripheral blood dendritic cells and monocytes" *Journal of Immunology* 151(12): 6840–52). It has long been known that by appropriate pre-treatment of a recipient animal or human with a variety of treatment protocols, long lasting tolerance (non-rejection) of the allo- and xenograft can be induced (Zimmerman, C. E., Stuart, F. P., et al. (1965) "Dog renal homografts prolonged by antigenic pretreatment" *Surgical Forum* 16: 267–9; and Sykes, M., Lee, L. A., et al. (1994) "Xenograft tolerance" *Immunological Reviews* 141: 245–76). The mechanism by which the tolerance is induced is as yet unclear. The induction of donor specific tolerance to an allo- or xenograft is the ultimate goal of transplantation immune modulation.

Although the effects and role of stress proteins in biological systems has been widely investigated in context of autoimmune disease (Lamb, J. R., Bal, V., et al. (1989) "Stress proteins may provide a link between the immune response to infection and autoimmunity" *Int. Immunol.* 1: 191–196) and cancer immunity (Srivastava, P. K., Heike, M. (1991) "Tumor-specific immunogenicity of stress-induced proteins: convergence of two evolutionary pathways of antigen presentation?" *Seminars in Immunology* 3(1): 57–64) it has not been the case for the possible involvement of stress proteins in the biology of transplant immunology. The majority of published works on the role of stress proteins in transplant immunology has focused on the demonstration of stress protein expression by grafted organs (Currie, R. W. (1987) "Effects of ischemia and perfusion temperature on the synthesis of stress-induced (heat shock) proteins in isolated and perfused rat hearts" *Journal of Molecular & Cellular Cardiology* 19(8): 795–808; Qian, J., Moliterno, R., et al. (1995) "Expression of heat shock proteins and lymphocyte reactivity in rat cardiac allografts undergoing cellular rejection" *Transplant Immunology*: In Press; and Davis, E. A., Wang, B. H., et al. (1995) "Induction of Heat Shock Protein in a Model of Acute Cardiac Allograft Rejection" *Personal Communication*). No such investigation of xenografts has been undertaken. The remaining published works focus on the demonstration of T-cell lymphocytes with specific reactivity against stress proteins and specifically heat shock proteins (Mycobacterial tuberculosis hsp71) and glucose regulated proteins (murine grp78) both of which are recombinant proteins expressed in an *E. coli* expression system. (Moliterno, R., Valdivia, L., et al. (1995) "Heat shock protein reactivity of lymphocytes isolated from heterotopic rat cardiac allografts" *Transplantation*: In Press; and Moliterno, R., Woan, M., et al. (1995) "Heat shock protein-induced T lymphocyte propagation from endomyocardial biopsies in heart transplantation" *Journal of Heart and Lung Transplantation*: In Press). On reinterpretation of these data it becomes clear that the reactivity of these T-lymphocytes propagated from allografts are in fact not directed to hsp or grp but to an unknown *E. coli* peptide contained in the stress protein. This is in concordance with the published function of the stress proteins in antigen presentation (DeNagel, D. C., and Pierce, S. K., (1993) "Heat shock proteins in immune responses" *Critical Reviews in Immunology* 13(1): 71–81; Lakey, E. K., Margoliash, E., et al. (1987) "Identification of a peptide binding protein that plays a role in antigen presentation" *Proc. Natl. Acad. Sci. USA* 84: 1659–1663; and Pierce, S. K. (1994) "Molecular chaperones in the processing and presentation of antigen to helper T cells" *Experientia* 50: 1026–1030).

SUMMARY OF THE INVENTION

A first aspect of the present invention is the application of stress proteins to modulate the immune response.

A second aspect of the present invention is the specificity of the tissue or cells from which these stress proteins are derived.

A third aspect of the present invention is the use of genetic engineering or recombinant techniques to enhance the expression of stress proteins.

A fourth aspect of the present invention is the use of genetic engineering or recombinant techniques to express stress proteins of a specific description along with any other specific proteins in an expression system, such as recombinant *E. coli* but not limited to *E. coli*.

A fifth aspect of the present invention is the description of specific stress protein candidates but not limited to those specific stress proteins.

A sixth aspect of the present invention is a pharmaceutical composition comprising a therapeutically effective amount of stress protein in a pharmaceutically acceptable formulation.

A seventh aspect of the present invention is a description of alternative methods to employ the effects of the described stress proteins in the modulation of the host immune response, besides in vivo administration of the stress proteins, such as in vitro pre-treatment of host, donor or third party donor derived cells or tissues.

DETAILED DESCRIPTION OF THE INVENTION

By administering specifically purified stress proteins derived from certain specific tissues, cells or genetically engineered or recombinant organisms, in an effective manner (which includes intravenous injection, subcutaneous or any other parenteral route, oral route, topical application and in vitro treatment of host, donor or third party donor tissues, cells or specialized immune system cells before administration of said tissues, cells or specialized immune system cells into the body of the host by any route) to humans or animals that may be in need of such immune response modulation such as those undergoing allo-, auto- or xeno-organ transplantation, the long-term survival of said transplanted organ will be improved without the need for indefinite conventional immunosuppressive therapy.

A description of specific tissues, cells or specialized immune system cells from which the specific stress proteins are to be derived in order to be effective follows. In the case of organ transplantation, whether it be allo- or xeno-transplantation, the specific tissues, cells or specialized immune system cells is required to be of donor specific or alternatively of donor syngeneic origin. The specific stress proteins are purified from these specific tissues, cells or specialized immune system cells by techniques and methods known to those skilled in the art of protein chemistry and protein purification, in such a way as not to destroy the biological activity of the stress proteins required to effect immune response modulation [Welch, 1982 #1227]. An example: By adding a ATP-binding step to the purification method of hsp72 the yield of purified protein could be greatly improved, this step however causes the stress protein to release any and all peptides bound to its peptide binding domain and would thereby lose its biological activity insofar as its ability to modulate the immune response is concerned.

Since the active ingredient in the stress protein preparation used to modulate the immune response in the host is any one number of a variety of specific stress proteins, the increased expression of certain specific stress proteins in any given tissue or cell culture system can be achieved by genetic engineering or recombinant techniques. This would still require the tissue or cell culture system be of donor or donor syngeneic origin.

By applying genetic engineering and recombinant techniques the expression of other donor specific or donor syngeneic proteins can be achieved in an expression system. This expression system is not required to be of human or animal origin, but can be of any suitable origin such as *E. coli* but not limited to this organism. The expression of stress proteins of human or animal origin in the same expression system achieves binding of peptides, including the human or animal transfected protein peptide, to human or animal stress proteins. This method is applicable to stress protein production for application in transplant immune response modulation.

The specific proteins called stress proteins in the present invention is a group of highly conserved proteins where homologous proteins from bacteria to man show very high degrees of sequence homologies and even higher functional homology. These proteins are characterized by their low expression in the normal cell and by the preferential increase in expression of these proteins under conditions of stress to the cell. Some members of this group of proteins are however expressed in high levels in the normal cell and are called constitutively expressed heat shock proteins (or stress proteins). The term stress protein is a collective term to describe all heat shock proteins (describing the stress heat, first found to upregulate expression of this sub-group) and glucose regulated proteins (glucose starvation was the initial stress described resulting in upregulation of this subgroup of stress proteins) and all constitutively expressed heat shock proteins (proteins found to have very similar amino acid sequences but abundantly expressed in the normal cell). Each of the mentioned subgroups are further subdivided by their approximate molecular weight. Certain stress proteins are more frequently found in certain subcellular compartments and are therefore named according to their physical location in the cell. Due to the complex nomenclature and often uncertain origins of a newly purified and described protein, some proteins belonging to the stress protein group are named differently. An example of a full name of a stress protein is: Cytosolic HSP72—describing a 72 kDa heat shock protein, predominantly found in the cytosol.

All stress proteins share a common structure including a non-variable ATP binding carboxyl terminal and a highly variable peptide binding amino terminal. Binding of peptides to the aminoterminal is dependent on ATP binding to the carboxy terminal. The various subgroups of stress proteins have different affinities for peptides of differing structures. Their dependency on ATP to release peptides also differ. The size of peptides bound to the various stress proteins range from 7 to 8 amino acids to very large molecules.

The specific molecules involved in antigen presentation are: HSP72 and animal, bacterial and fungal homologues, HSC73 and animal, bacterial and fungal homologues, GRP94 and animal, bacterial and fungal homologues, GRP75 and animal, bacterial and fungal homologues, GRP78 and animal, bacterial and fungal homologues, Erp72 and animal, bacterial and fungal homologues and PBP72/74 and animal, bacterial and fungal homologues. Other molecules belonging to the stress protein group involved in antigen presentation, yet undiscovered, are also included in this application of stress proteins in the modulation of the immune response as described in this invention.

The present invention describes the application for stress proteins in a role that will utilize their ability to modulate various immune responses. It is intended that any effective amount of stress proteins derived from material described in this present invention and included in any pharmaceutical composition be embraced by this invention. An exemplary excipient is buffered saline; typical dose per patient treatment ranges between 10 $\mu$g and 1 mg.

Alternative methods of utilizing the presently invented application of stress proteins include, but is not limited to the following: The successful application of stress proteins in the modulation of the immune response in respect to transplantation is dependent on placing the specific stress proteins in such a position or environment that it will be preferentially ingested by specific subsets of antigen presentation cells of the host body, or by effectively modifying the functionational capabilities of said antigen presenting cells through the concomitant use of additional molecules such as monoclonal antibodies or soluble receptor analogues. This can be achieved by binding the stress proteins to other molecules known to specifically target certain subsets of antigen presentation cells, such as monoclonal antibodies, but not limited to monoclonal antibodies. This preferential ingestion of the said stress proteins by specific subsets of antigen presentation cells of the host body can also be achieved by in vitro culturing of the specific stress proteins with appropriate subsets of antigen presentation cells. These pre-treated antigen presentation cells will then administered to the intended recipient of the treatment. This preferential ingestion of the said stress proteins by specific subsets of antigen presentation cells of the host body can also be achieved by injecting or introducing the said stress proteins into a privileged site in the host body, such as intravenously, rather than intracutaneously or subcutaneously. The present invention does however not include introduction of the said stress proteins or pre-treated cells or modified stress protein molecules into the thymus of the host human or animal.

The novelty of this application of stress proteins lies in the recognition of a novel process involved in the rejection of grafts including allo-, auto- and xenografts.

I claim:

1. A method for modulating a tissue graft immune response comprising the step of contacting an antigen presenting cell with an effective amount of a stress protein bound to an antigen.

2. A method for modulating a tissue graft immune response as claimed in claim 1, further comprising contacting immune system cells with an additional molecule selected from the group consisting of a monoclonal antibody and a soluble receptor analogue such that immune response to said antigen is reduced.

3. A method for modulating a tissue graft immune response as claimed in claim 1, wherein the antigen is purified from one of a graft, from a graft donor or from a donor syngeneic origin and the method further comprises the step of binding the antigen to the stress protein.

4. A method for modulating a tissue graft immune response as claimed in claim 1, wherein the stress protein bound to an antigen is purified from a graft, from a graft donor or from a donor syngeneic origin.

5. A method for modulating a tissue graft immune response as claimed in claim 1, comprising administering into an animal or human patient one or more unit doses of a stress protein bound to an antigen in combination with a pharmaceutically acceptable excipient.

6. A method for modulating a tissue graft immune response as claimed in claim 5, wherein said modulation prevents graft rejection, comprising the steps of:

a. administering to the animal or human patient a stress protein bound to an antigen of the graft; and b. administering to a patient an additional molecule selected from the group consisting of a monoclonal antibody and a soluble receptor analogue to achieve tolerance of the graft.

7. A method for modulating a tissue graft immune response as claimed in claim 1, wherein said stress protein is characterized by its nonvariable ATP binding carboxyl terminal and a highly variable peptide binding amino terminal and said effective amount is between about 10 $\mu$g and 1 mg per patient treatment.

8. A method as claimed in claim 1, wherein said stress protein is exogenous and furthermore is purified from a source selected from the group consisting of donor specific cells and donor syngeneic cells.

9. A pharmaceutical composition comprising a stress protein bound to an antigen and a pharmaceutically acceptable excipient.

10. A pharmaceutical composition as claimed in claim 9, wherein said stress protein comprises a nonvariable ATP binding carboxyl terminal and a highly variable peptide binding amino terminal.

11. A pharmaceutical composition as claimed in claim 9, wherein the stress protein bound to an antigen is co-purified from a graft such that the stress protein does not release the antigen.

12. A pharmaceutical composition as claimed in claim 9, wherein said stress protein is purified from third party tissues or cells which have been genetically engineered or otherwise manipulated to produce stress proteins and to express donor antigens.

13. A pharmaceutical composition as claimed in claim 12, wherein said third party tissues or cells are of human origin.

14. A pharmaceutical composition as claimed in claim 12, wherein said third party tissues or cells are of animal origin.

15. A pharmaceutical composition as claimed in claim 12, wherein said third party tissues are of non-animal origin.

16. A method of making a stress protein comprising purifying from donor specific and/or donor syngeneic cells a protein characterized by its nonvariable ATP binding carboxyl terminal and a highly variable peptide binding amino terminal, wherein said protein is bound to an antigeneic peptide.

* * * * *